United States Patent
Nakamura (10) Patent No.: US 8,529,061 B2
(45) Date of Patent: Sep. 10, 2013

(54) EYE REFRACTIVE POWER MEASUREMENT APPARATUS

(75) Inventor: Kenji Nakamura, Aichi (JP)

(73) Assignee: Nidek Co., Ltd., Aichi (JP)

( * ) Notice: Subject to any disclaimer, the term of this patent is extended or adjusted under 35 U.S.C. 154(b) by 274 days.

(21) Appl. No.: 12/958,219

(22) Filed: Dec. 1, 2010

(65) Prior Publication Data

US 2011/0128498 A1 Jun. 2, 2011

(30) Foreign Application Priority Data

Dec. 2, 2009 (JP) ................................. 2009-274058

(51) Int. Cl.
*A61B 3/10* (2006.01)
*A61B 3/00* (2006.01)

(52) U.S. Cl.
USPC .......................................... 351/206; 351/246

(58) Field of Classification Search
USPC .......................... 351/205, 206, 211, 212, 246
See application file for complete search history.

(56) References Cited

U.S. PATENT DOCUMENTS

| 5,071,245 A | * | 12/1991 | Fukuma et al. ................ 351/211 |
| 7,416,301 B2 | | 8/2008 | Hanebuchi et al. |
| 7,452,078 B2 | | 11/2008 | Isogai |
| 7,677,727 B2 | | 3/2010 | Shimizu et al. |

FOREIGN PATENT DOCUMENTS

| JP | 2005185523 A | 7/2005 |
| JP | 2007089715 A | 4/2007 |
| JP | 2009078129 A | 4/2009 |

* cited by examiner

*Primary Examiner* — Mahidere Sahle
(74) *Attorney, Agent, or Firm* — Lowe Hauptman & Berner, LLP (57) ABSTRACT

An eye refractive power measurement apparatus includes a measurement optical system, a calculator and an output unit. The measurement optical system projects measurement light onto a fundus of an examinee's eye, extracts the measurement light reflected on the fundus as ring-shaped light, and causes an imaging device to capture a ring-shaped image. The calculator measures eye refractive power of the examinee's eye, based on the ring-shaped image captured by the imaging device, specifies a position of the ring-shaped image to calculate a measured line of the image, performs approximate processing on the measured line to calculate an approximate curve, and calculates a displacement between the measured line and the approximate curve in a meridian direction for each divided region. The output unit outputs a measurement result of the eye refractive power and a calculation result of the displacement in each divided region.

13 Claims, 5 Drawing Sheets

EYE REFRACTIVE POWER MEASUREMENT APPARATUS

CROSS-REFERENCE TO RELATED APPLICATION

This application is based on Japanese Patent Application No. 2009-274058 filed with the Japan Patent Office on Dec. 2, 2009, the entire content of which is hereby incorporated by reference.

BACKGROUND

1. Technical Field

The present invention relates to an eye refractive power measurement apparatus which measures refractive power of an examinee's eye.

2. Related Art

There is known an eye refractive power measurement apparatus which projects measurement light onto a fundus of an examinee's eye, extracts the light reflected on the fundus as a ring image, causes a two-dimensional imaging device to capture this ring image, and measures eye refractive power, based on the captured ring image. In such an apparatus, a reliability coefficient is displayed on a monitor (refer to Patent Document 1). The reliability coefficient is obtained in such a manner that each of differences between a measured line, obtained by sequentially detecting an edge of the ring image per one degree over 360 degrees, and an elliptical approximation of the measured line is calculated, and these differences are added up.

The document that describes the related art is listed below.
Patent Document 1: JP 2007-089715 A (U.S. Pat. No. 7,452,078)

However, the conventional apparatus shows a displacement level in the entire eye by means of the reliability coefficient. Therefore, when a certain region has irregular astigmatism, it is difficult to specify this region having irregular astigmatism. Further, although there is a normal region where irregular astigmatism is not likely to exist, a low reliability coefficient is calculated due to the partial region having irregular astigmatism. It is to be noted that the same thing holds true for a case where a given region of a crystalline lens has cataract opacity.

SUMMARY

In view of the above problems, a technical object of the present invention is to provide an eye refractive power measurement apparatus for allowing an examiner to specify with ease an error region and a region other than the error region in a measurement region.

To solve the above problem, the present invention has the following configuration.

An eye refractive power measurement apparatus includes a measurement optical system, a calculator and an output unit. The measurement optical system projects measurement light onto a fundus of an examinee's eye, extracts the measurement light reflected on the fundus as ring-shaped light, and causes an imaging device to capture a ring-shaped image. The calculator measures eye refractive power of the examinee's eye, based on the ring-shaped image captured by the imaging device, specifies a position of the ring-shaped image to calculate a measured line of the image, performs approximate processing on the measured line to calculate an approximate curve, and calculates a displacement between the measured line and the approximate curve in a meridian direction for each divided region. The output unit outputs a measurement result of the eye refractive power and a calculation result of the displacement in each divided region.

According to the present invention, an examiner can specify with ease an error region and a region other than the error region in a measurement region.

BRIEF DESCRIPTION OF THE DRAWINGS

The foregoing and other objects, features, aspects and advantages of the invention will become more apparent from the following detailed description when taken in conjunction with the accompanying drawings, in which.

DESCRIPTION OF EMBODIMENTS

Preferred embodiments of the present invention will be described below with reference to the accompanying drawings, in which like reference characters designate similar or identical parts throughout the several views thereof.

Figure 1:
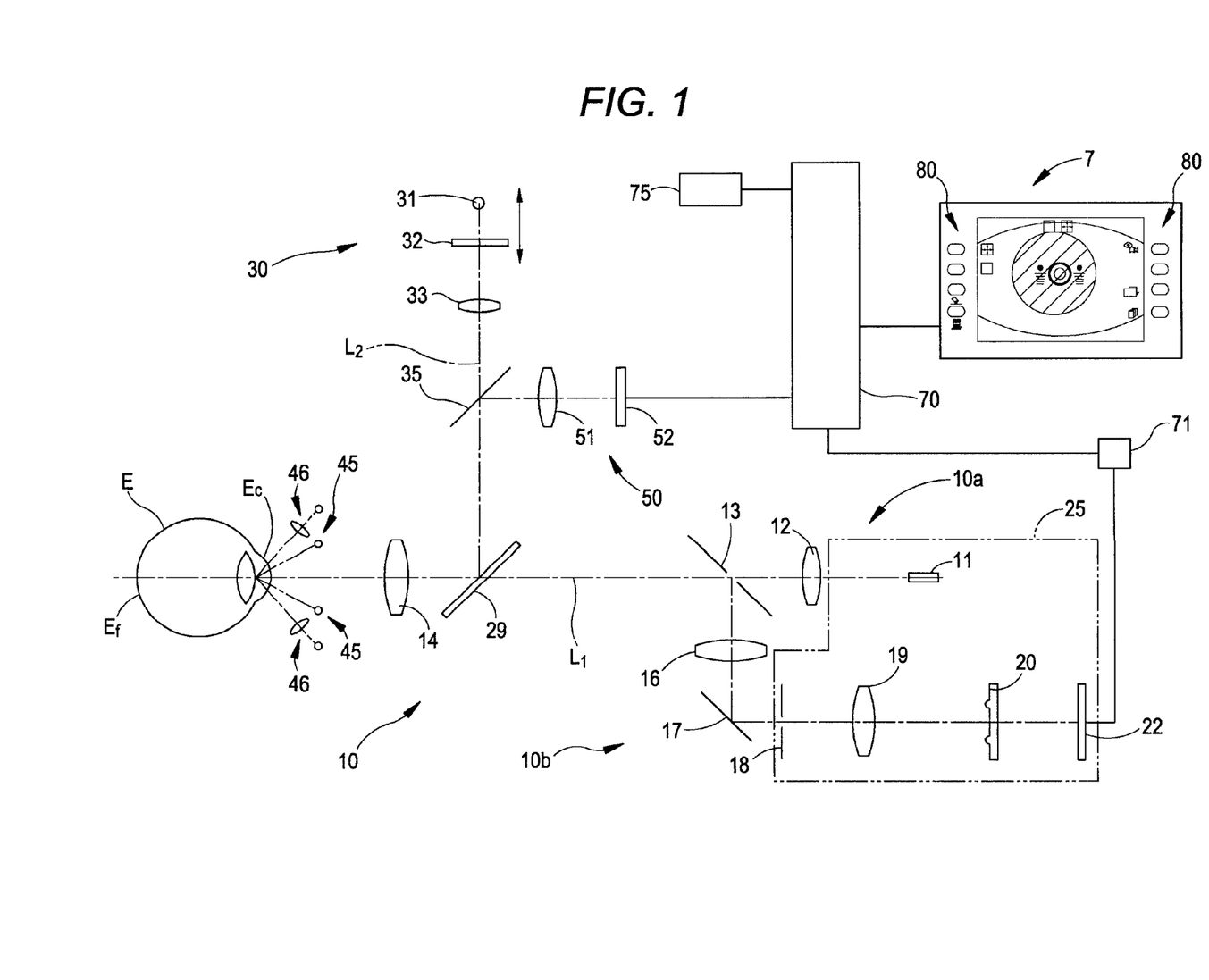
FIG. 1 is a view illustrating a schematic configuration of an optical system and a control system in an apparatus according to one embodiment of the present invention.

FIG. 1 is a view illustrating a schematic configuration of an optical system and a control system in an apparatus according to one embodiment of the present invention. A measurement optical system 10 is configured with a projecting optical system 10a and a light receiving optical system 10b. The projecting optical system 10a projects a spot-shaped measurement target onto a fundus Ef of an eye E via a center of a pupil of the eye E. The light receiving optical system 10b extracts light, reflected from the fundus Ef, in a ring shape via a periphery of the pupil of the eye E, and causes a two-dimensional imaging device to capture (receive) a ring-shaped image.

The projecting optical system 10a includes a measurement light source 11, a relay lens 12, a hole mirror 13, and an objective lens 14. These members 11 to 14 are arranged on an optical axis L1 of the measurement optical system 10. The measurement light source 11 is located in an optically conjugated position with the fundus Ef of an emmetropic eye.

Further, an opening of the hole mirror 13 is located in an optically conjugated position with the pupil of the eye E.

The light receiving optical system 10b shares the objective lens 14 and the hole mirror 13 of the projecting optical system 10a with the projecting optical system 10a. Further, the light receiving optical system 10b includes a relay lens 16 and a total reflection mirror 17 which are arranged on the optical axis L1 in a reflecting direction of the mirror 13. Moreover, the light receiving optical system 10b includes a light receiving diaphragm 18, a collimator lens 19, a ring lens 20 and a two-dimensional imaging device 22 made of an area CCD or the like. These members 18, 19, 20 and 22 are arranged on the optical axis L1 in a reflecting direction of the mirror 17. The light receiving diaphragm 18 and the imaging device 22 are located in optically conjugated positions with the fundus Ef. The ring lens 20 is configured with a lens part formed in a ring shape, and a light shielding part made up of a region other than the lens part which is subjected to coating for light shielding. The ring lens 20 is located in an optically conjugated position with the pupil of the eye E. An output from the imaging device 22 is input to a control part 70 via an image memory 71.

It is to be noted that the measurement optical system 10 is not limited to that described above, but a known configuration may be applied thereto. There is for example used a configuration where a ring-shaped measurement target is projected from the periphery of the pupil onto the fundus Ef, and fundus reflection light is extracted from the center of the pupil, so that the two-dimensional imaging device receives a ring-shaped image. There may be used a configuration where an intermittent ring image rather than a continuous ring image is extracted. There may be used a configuration where a fundus reflection image formed by spot images aligned in a substantially ring shape is extracted.

A dichroic mirror 29 is arranged between the objective lens 14 and the hole mirror 13. The dichroic mirror 29 guides fixation target light from a fixation target presenting optical system 30 to the eye E, while guiding reflection light from an anterior segment of the eye E toward an observing optical system 50. The dichroic mirror 29 allows light with a wavelength of measurement light, used in the measurement optical system 10, to pass therethrough.

The fixation target presenting optical system 30 includes a visible light source for presenting a fixation target, a fixation target plate 32 having a fixation target, a light projecting lens 33, the dichroic mirror 29 and the objective lens 14. The light source 31 and the fixation target plate 32 are shifted in a direction of an optical axis L2, to fog the eye E.

A ring target projecting optical system 45 and a distance target projecting optical system 46 are arranged in front of the anterior segment of the eye E. The projecting optical system 45 emits near-infrared light for projecting a ring target onto a cornea Ec of the eye E. The distance target projecting optical system 46 is arranged symmetrically to an observation optical axis. This projecting optical system 46 emits near-infrared light for projecting an infinity ring target onto the cornea Ec. The projecting optical system 46 is used for detecting the state of alignment with the eye in an operating distance direction. In addition, the projecting optical system 45 is also used as an anterior segment illumination for illuminating the anterior segment of the eye E. Further, the projecting optical system 45 can also be used as an target for measuring a cornea shape.

The observing optical system 50 shares the objective lens 14 and the dichroic mirror 29 described above with the fixation target presenting optical system 30. Further, the observing optical system 50 includes a half mirror 35, an imaging lens 51, and a two-dimensional imaging device 52. An output from the imaging device 52 is input to the control part 70. Thus, an anterior segment image of the eye E is captured by the two-dimensional imaging device 52, and displayed on the monitor 7. It is to be noted that this observing optical system 50 also serves as an optical system to detect an alignment target image formed on the cornea of the eye E. The control part 70 detects a position of the alignment target image.

The calculation controlling part 70 (hereinafter, referred to as control part 70) is connected with the image memory 71, the imaging device 52, a memory 75, the monitor 7, a switch part 80, and the like. The switch part 80 has a plurality of switches, and used for a variety of settings in measurement. The control part 70 controls the entire apparatus while calculating values of eye refractive power, a cornea shape, and the like. It should be noted that the memory 75 stores an operation program for calculating eye refractive power, based on a ring image, and the like.

A measurement operation of the apparatus having the foregoing configuration is described. First, an examinee's face is fixed to a face supporting part, not illustrated. Next, after the examinee has been directed to fixate the fixation target plate 32, alignment with the examinee's eye is performed.

The control part 70 makes the light source 11 to light up, based on an input of a measurement starting signal. The measurement light emitted from the light source 11 is projected onto the fundus Ef via from the relay lens 12 to the objective lens 14, and forms a point light source image in a spot shape.

Light of the point light source image formed on the fundus Ef is reflected and scattered, and emitted from the examinee's eye E, to be collected by the objective lens 14. Subsequently, the light is collected again on an opening of the light receiving diaphragm 18 via from the dichroic mirror 29 to the total reflection mirror 17, and turned to substantially parallel light by the collimator lens 19 (in the case of the emmetropic eye). This substantially parallel light is extracted by the ring lens 20 as ring-shaped light. This ring-shaped light is received in the imaging device 22 as a ring image.

In this measurement, preliminary measurement of the eye refractive power is first performed. Based on a result of this preliminary measurement, the light source 31 and the fixation target plate 32 are shifted in the direction of the optical axis L2 to fog the examinee's eye E. Thereafter, measurement of the eye refractive power is performed on the fogged examinee's eye.

Figure 2:
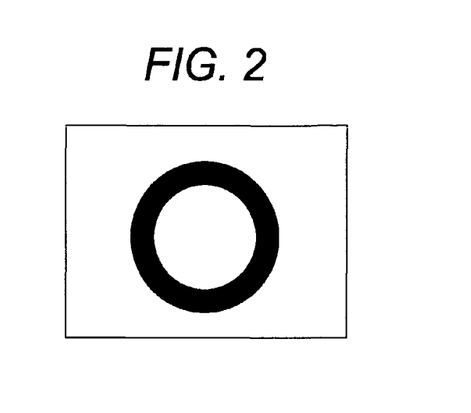
FIG. 2 is a view illustrating a ring image captured by an imaging device of an eye refractive power measurement optical system at the time of measurement.

FIG. 2 illustrates a ring image captured by the imaging device 22 at the time of measurement. An output signal from the imaging device 22 is stored as image data (measurement image) into the image memory 71. Thereafter, the control part 70 specifies (detects) a position of the ring image in each meridian direction, based on the measured image stored in the image memory 71. In this case, the control part 70 specifies the position of the ring image by edge detection. In addition, the position of the ring image may be specified with a reference of a midpoint of a cut position in a waveform of a luminance signal cut by a predetermined threshold, a peak of the waveform of the luminance signal, a position of the center of gravity of the luminance signal, or the like. Next, the control part 70 obtains an ellipse by approximation using a least-squares method or the like, based on the specified position of the ring image. The control part 70 then obtains a refraction error in each meridian direction from the elliptical shape obtained by approximation. Thereafter, the control part 70 calculates an eye refraction value and respective values of S (sphere power), C (cylinder power), and A (astigmatic axial angle) of the examinee's eye, based on the refraction errors, and displays calculation results (measurement results) on the monitor 7. Further, the control part 70 calculates a reliability coefficient, and displays calculation results (measurement results) on the monitor 7.

Figure 3:
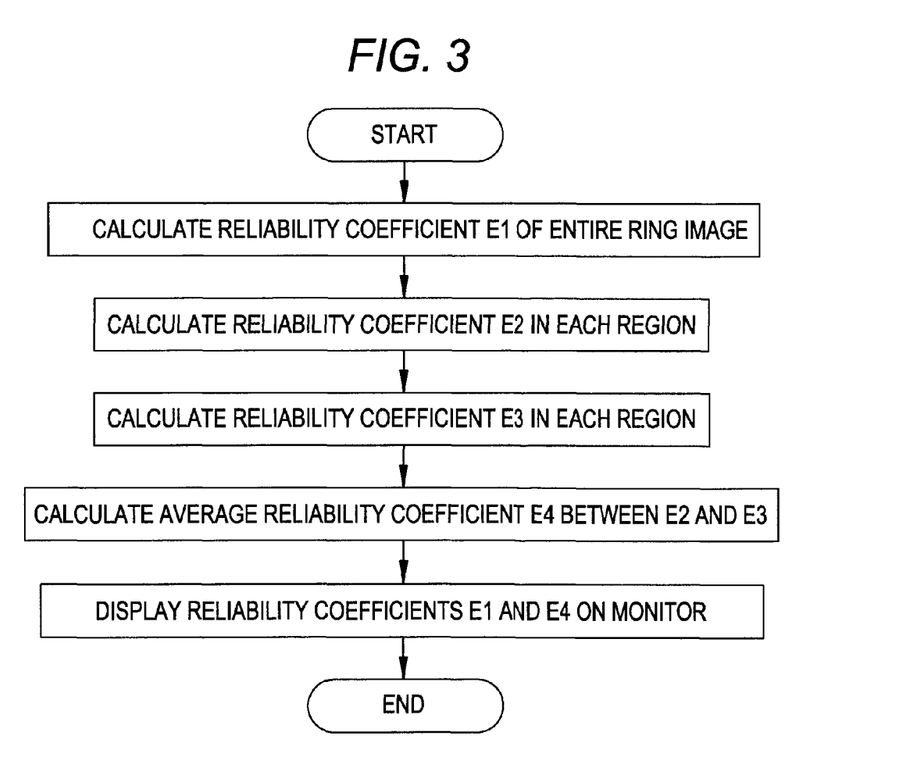
FIG. 3 is a flowchart of a procedure for calculating a reliability coefficient.

Hereinafter, a reliability coefficient calculating technique according to the present embodiment is described based on a flowchart of FIG. 3. First, the control part 70 calculates a reliability coefficient E1 of the entire ring image. The control part 70 sequentially detects an edge in each meridian direction per one degree over 360 degrees with a central coordinate of the ring image as a reference. The control part 70 then calculates a difference between a measured line obtained by edge detection and an ellipse obtained by elliptically approximating the measured line. Subsequently, the control part 70 adds up results of calculation of the differences for all directions over 360 degrees.

Figure 4:
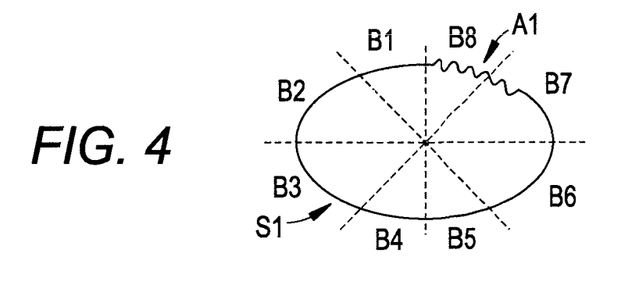
FIG. 4 is a view illustrating a ring image obtained in the case of the existence of a partial refractive error in a jagged shape.
Figure 5:
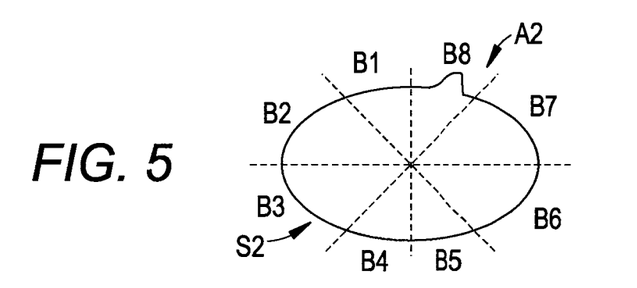
FIG. 5 is a view illustrating a ring image obtained in the case of the existence of a refractive error due to one extremely large irregularity.

As illustrated in FIG. 4, the ring image may have a standard part S1 in a similar shape to the approximated elliptical curve, and a partial refractive error A1 in a jagged shape. In this case, when a reliability coefficient is calculated as a whole, the existence of an error part is buried. It is consequently difficult to specify a region of the error part, as well as determining the presence or absence thereof. In FIG. 5, the ring image may have a standard part S2 and a refractive error A2 with one extremely large irregularity. The case of this image also has a similar problem to the above.

Meanwhile, the standard parts S1 and S2 in the ring images in FIGS. 4 and 5 have shapes almost close to the elliptical approximate curve. However, the existence of the standard part (normal part) is buried in the ring image as the entire approximation. It is consequently difficult to specify a region of the standard part, as well as determining the presence or absence thereof. This is due to inclusion of the refractive errors A1 and A2 in the objects for approximation processing.

Hence, the control part 70 calculates a displacement between a measured line, obtained by detecting a position of the ring image, and an approximate curve, obtained by performing approximate processing on the measured line, in the meridian direction for each of predetermined divided regions B1 to B8. The control part 70 then calculates reliability coefficients (E2, E3, E4) in each of the divided regions B1 to B8 (see FIGS. 4 and 5). It is to be noted that in FIGS. 4 and 5, the measured line of the ring image is divided at each predetermined angle (every 45 degrees).

More specifically, in the case of obtaining the reliability coefficient E2, the control part 70 calculates a measured line by means of edge detection in each of the divided regions B1 to B8. Further, the control part 70 calculates an approximate curve (divided approximate curve) based on the measured line in each of the divided regions B1 to B8. The control part 70 then calculates a difference between each approximate curve and the measured line corresponding thereto in the meridian direction for each of the divided regions B1 to B8. Thereafter, the control part 70 obtains the reliability coefficient E2 for each of the divided regions B1 to B8.

Figure 6:
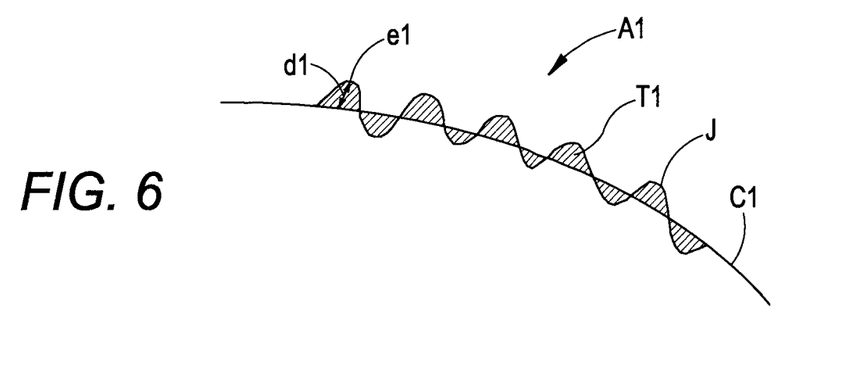
FIG. 6 is an enlarged view of a refractive error A1 in FIG. 4.

The above processing is described taking, as an example, FIG. 6 which is an enlarged view of the refractive error A1 of the ring image illustrated in FIG. 4. For example, the control part 70 adds up differences T1 (shaded portions), obtained by comparing an approximate curve C1 and a measured line J by means of edge detection in the divided region B8. Herein, the difference T1 is obtained in such a manner that displacement amounts d1 to dn between respective edge positions e1 to en on the measured line J and the approximate curve C1 (see FIG. 6) are squared. A value obtained by dividing a result of adding up the respective values, obtained by squaring, by the number of additions is calculated as the difference T1.

Specifically, the difference T1 is expressed by: $T1=(d1^2 + d2^2 + \ldots dn^2)/n$. The control part 70 then converts (classifies) the difference T1 to the reliability coefficient E2 (nine levels from 1 to 9). It is to be noted that by using a similar technique, the control part 70 calculates the reliability coefficient E2 in the other divided regions B1 to B7.

In the case of calculating the reliability coefficient E2 in each divided region with respect to the ring image illustrated in FIG. 4 as described above, the difference T1 is small in the divided regions B1 to B6 corresponding to the standard part S1 since being not affected by the refractive error A1. Therefore, the reliability coefficients in these regions are high. These regions are thus specified as portions where irregular astigmatism is not likely to exist.

On the other hand, the respective reliability coefficients in the divided regions B7 and B8 corresponding to the refractive error A1 are low with the difference T1 being large. Accordingly, such regions as the divided regions B7 and B8 with a large displacement appearing between the measured line and the approximate curve are specified as portions where a local refractive error (irregular astigmatism) is likely to exist.

Subsequently, the control part 70 obtains the reliability coefficient E3 in each of the divided regions B1 to B8, based on the approximate curve C1 calculated for each of the divided regions B1 to B8, and an elliptical approximate curve (overall approximate curve) O1 calculated from the entire ring image.

Figure 7A:
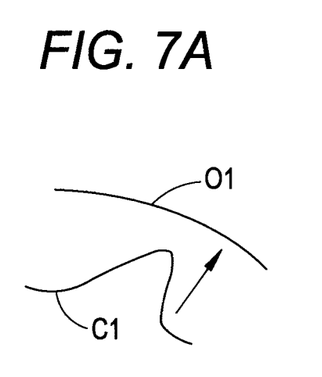
FIGS. 7A and 7B are views illustrating a procedure for virtually shifting an approximate curve C1 toward an elliptical approximate curve O1 in a predetermined meridian direction, to bring the approximate curve C1 into contact with this elliptical approximate curve O1.
Figure 7B:
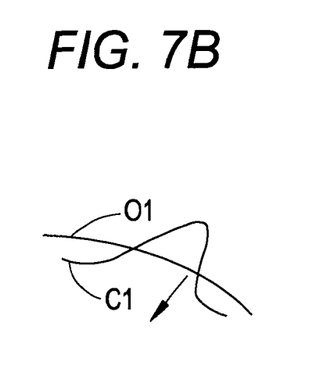

For example, as illustrated in FIGS. 7A and 7B, the approximate curve C1 is virtually shifted in a predetermined meridian direction (e.g., a direction at 67.5 degrees in the case of the divided region B8) so as to approach the elliptical approximate curve O1. Positions of the approximate curve C1 and the elliptical approximate curve O1 where the displacement therebetween is minimal are obtained, and a difference between the approximate curve C1 and the elliptical approximate curve O1 at those positions is obtained. The reliability coefficient E3 in each divided region is then obtained. In this case, the elliptical approximate curve O1 and the approximate curve C1 are in the state of being in contact with or crossing each other.

Figure 8:
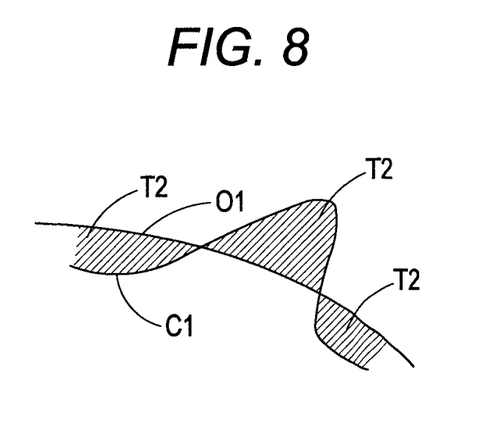
FIG. 8 is an enlarged view of a refractive error A2 in FIG. 5.

The above processing is described taking, as an example, FIG. 8 which is an enlarged view of the refractive error A2 of the ring image illustrated in FIG. 5. For example, the control part 70 adds up differences T2 (shaded portions), obtained by comparing the approximate curve C1 and the elliptical approximate curve O1 in the divided region B8. The control part 70 then converts the difference T2 to the reliability coefficient E3 (nine levels from 1 to 9). It is to be noted that by using a similar technique, the control part 70 calculates the reliability coefficient E3 in the other divided regions B1 to B7.

In this case, the difference T2 is small in the divided regions B1 to B7 corresponding to the standard part S2 since being not affected by the refractive error A2. Therefore, the reliability coefficients in these regions are high. These regions are thus specified as portions where irregular astigmatism is not likely to exist.

On the other hand, the reliability coefficient in the divided region B8 corresponding to the refractive error A2 is low with the difference T2 being large. Accordingly, such a region as the divided region B8 with a large displacement appearing between the elliptical approximate curve O1 and the approximate curve C1 is specified as a portion where a local refractive error (irregular astigmatism) is likely to exist.

Figure 9:
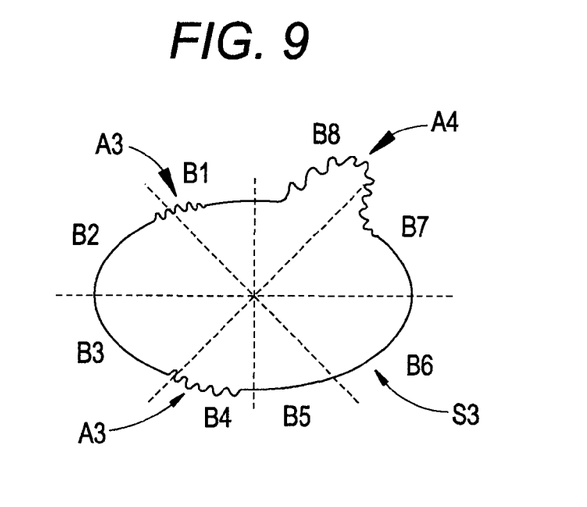
FIG. 9 is a view illustrating a ring image obtained in the case of the existence of both a partial refractive error in a jagged shape and one extremely large refractive error.

Furthermore, when the ring image is a ring image as illustrated in FIG. 9 which has two kinds of irregular astigmatism illustrated in FIGS. 4 and 5, the control part 70 can perform arithmetic processing by means of the foregoing flows to obtain more detailed irregular astigmatism information. For example, in a divided region having a partial refractive error A3 in a jagged shape, the control part 70 executes the arithmetic processing for the reliability coefficient E2. As a result, a reliability coefficient for this divided region is calculated to be low. Further, this arithmetic processing leads to specification that irregular astigmatism exist in the divided regions B1 and B4. Moreover, in a divided region having a refractive error A4 with partial and extreme irregularity, a reliability coefficient is calculated to be low by the arithmetic processing for the reliability coefficient E3. Further, this processing leads to specification that irregular astigmatism exists in the divided regions B7 and B8. In addition, the reliability coefficients E2 and E3 calculated concerning the other divided regions are relatively high.

After calculation of the reliability coefficients E1 to E3 in such a manner as above, the control part 70 obtains the reliability coefficient E4 as an average value of the reliability coefficient E2 and the reliability coefficient E3 with regard to the respective divided regions B1 to B8. It is to be noted that the control part 70 may regard the higher coefficient between E2 and E3 as the reliability coefficient E4.

Figure 10:
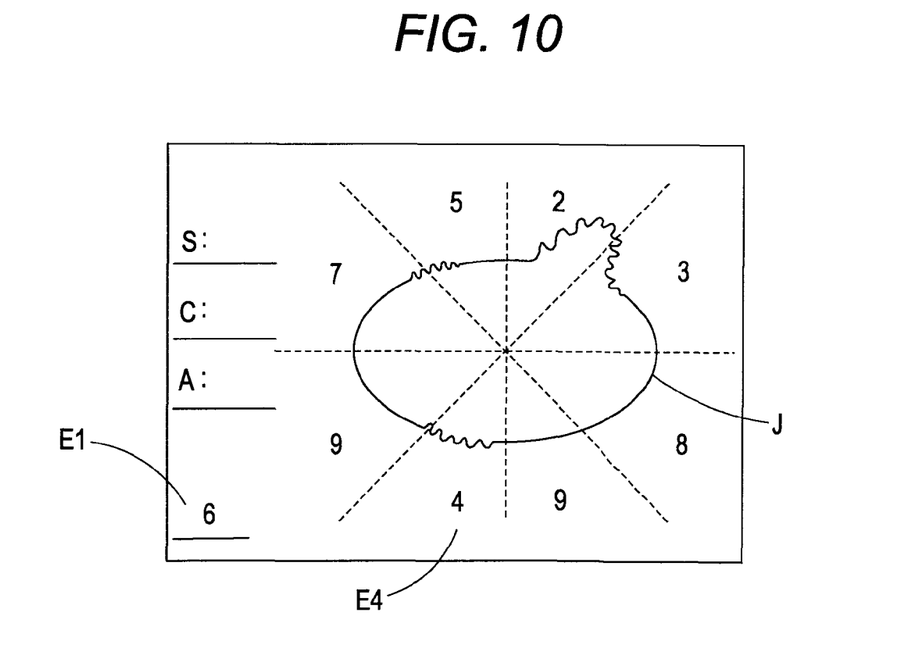
FIG. 10 is a view illustrating a screen example of a reliability coefficient display screen.

When the examiner selects a reliability coefficient display screen selection switch (not illustrated), an operation signal is output from this selection switch toward the control part 70. The control part 70 switches a display screen of the monitor 7 from a measurement result display screen to a reliability coefficient display screen. In the reliability coefficient display screen, for example as illustrated in FIG. 10, the control part 70 displays S, C, A, the overall reliability coefficient E1 and the measured line J (measured image) by means of edge detection on the monitor 7. Further, the control part 70 displays each of the divided regions B1 to B8 in the measured image and the reliability coefficient E4 in each of the divided regions on the monitor 7 in a mutually corresponding state. It is to be noted that the numeric range of the reliability coefficient is indicated, for example, by levels 1 to 9. Moreover, the measured line J may be a raw image of the ring image.

As thus described, outputting a reliability coefficient for each divided region allows the examiner to check the reliability coefficient in each region. The examiner can then grasp a position of irregular astigmatism which has been insoluble by use of a reliability coefficient based on the entire ring image. Hence the examiner can determine which region (a region in which meridian direction) has an error.

Thus, for example, the examiner can get aware of a local error region at the time of measuring eye refractive power. This enables early detection of a lesion.

Further, even when the overall reliability coefficient E1 is low, the examiner can recognize the existence of a divided region where the reliability coefficients E2 to E4 in each region have been calculated to be high. The examiner can then see the possibility that at the time of correcting refraction by means of eyeglasses or the like, the correction can be made using a region with a little irregular astigmatism.

In the foregoing description, the technique is described which specifies a region having irregular astigmatism and a region other than the region in a measurement region. However, a similar effect can be obtained also when the above technique is employed in the case of the existence of cataract opacity in a given region of a crystalline lens. Specifically, in a region where cataract opacity exists, the ring image is formed in a jagged shape and the reliability coefficient E2 thus decreases. For this reason, calculating the reliability coefficient E2 for each divided region specifies an error region and a region other than the error region in the measurement region.

In the foregoing description, the reliability coefficients E1, E2 and E3 are calculated in this order, but not limited thereto. In performing the arithmetic processing for E1 to E3, the order of the arithmetic processing is not necessarily considered.

In the foregoing description, the eight divided regions divided at every 45 degrees are applied as the divided regions in calculating the reliability coefficients E2 and E3, but not limited thereto. For example, twelve divided regions divided at every 30 degrees, or the like, may be employed.

In the foregoing description, when the refractive error A2 has occurred due to one extremely large irregularity, in order to obtain the reliability coefficient E3, an approximate curve in each region is superimposed on an elliptical curve obtained by approximating the entire ring image, to calculate a difference therebetween. However, the technique for obtaining the reliability coefficient E3 is not limited thereto.

For example, a displacement is calculated between a central coordinate of an elliptical curve, obtained by performing elliptical approximation processing on the entire ring image, and a central coordinate of an elliptical curve, obtained by performing elliptical approximation processing concerning each divided region. The reliability coefficient E3 may be calculated using this displacement. In this case, the larger the displacement is, the lower the reliability coefficient E3 is.

In the foregoing description, after calculation of the reliability coefficients E2 and E3, the average reliability coefficient E4 therebetween is displayed on the monitor 7, but not limited thereto. For example, values that can reflect reliability coefficients in partial regions, such as both the reliability coefficients E2 and E3, may be displayed on the monitor 7.

At the time of obtaining the reliability coefficient E3, the relative positions of the elliptical approximate curve O1, obtained from the entire ring image, and the approximate curve C1, calculated for each divided region, in the meridian direction may be virtually changed. In other words, the elliptical approximate curve O1 may be virtually shifted to the approximate curve C1. Alternatively, the measured line may be used in place of the approximate curve C1.

In the foregoing example, at the time of obtaining the reliability coefficient E3, positions of the approximate curve C1 and the elliptical approximate curve O1 where the displacement therebetween is minimal are obtained to specify a local refractive error with good accuracy, but not limited thereto. The elliptical approximate curve O1 and the approximate curve C1 may be brought into contact with or crossing each other. Thereafter, the reliability coefficient E3 may be calculated based on a displacement between both curves in that state. Also in this case, a certain effect can be obtained.

Further, the technique for obtaining the reliability coefficient for each divided region is not limited to the foregoing technique. The measured line of the entire ring image may be elliptically approximated, to calculate an elliptical approximate curve, and a displacement between the measured line and the elliptical approximate curve of the entire ring image may be calculated for each divided region.

In the foregoing example, the reliability coefficient is output by the numeric levels (e.g., nine levels from 1 to 9). However, the output of the reliability coefficient needs not to be limited thereto so long as being able to indicate the degree of reliability of measurement. For example, the degree of reliability may be expressed by levels using colors. Further, the degree of reliability may be output by graphics such as scaling gauge. Moreover, a measurement result of the degree of reliability may be printed out with a printer.

Furthermore, as illustrated in FIG. 10, graphics including the measured line J and the reliability coefficients in the respective divided regions B1 to B8 may be superimposed on an anterior segment image. Moreover, such a display image may be printed out on paper.

In the foregoing embodiment, moreover, this apparatus (the control part 70) is configured to calculate eye refractive power. Alternatively, this apparatus may be configured to merely detect an error region on an examinee's eye. Specifically, the apparatus according to the embodiment of the present invention may be configured as an error detection apparatus for extracting, as a ring image, reflected light from an examinee's eye and detecting an error region on the examinee's eye, based on the ring image. This error detection apparatus may include a calculator that acquires a measured line corresponding to an edge of the ring image, divides the measured line into predetermined divided regions, performs approximate processing on the measured line to calculate an approximate curve, calculates a displacement between the measured line and the approximate curve for each divided region, and detects an error state in each divided region, based on the displacement.

While the invention has been illustrated and described in detail, the foregoing description is in all aspects illustrative and not restrictive. It is therefore understood that numerous modifications and variations can be devised without departing from the spirit and scope of the invention.

What is claimed is:

1. An eye refractive power measurement apparatus comprising:
    a measurement optical system configured to project measurement light onto a fundus of an examinee's eye, to extract the measurement light reflected on the fundus as ring-shaped light, and to cause an imaging device to capture a ring-shaped image;
    a calculator configured to measure eye refractive power of the examinee's eye, based on the ring-shaped image captured by the imaging device, by
        specifying a position of the ring-shaped image to calculate a measured line of the image,
        performing approximate processing on the measured line to calculate an approximate curve, and
        calculating a displacement between the measured line and the approximate curve in a meridian direction for each divided region of the ring-shaped image; and
    an output unit configured to output a measurement result of the eye refractive power and a calculation result of the displacement in each divided region.

2. The eye refractive power measurement apparatus according to claim 1, wherein
    the output unit is configured to classify the calculation result of the displacement in each divided region by a level, and to output a classification result as a degree of reliability in each divided region.

3. The eye refractive power measurement apparatus according to claim 1, wherein
    the output unit is configured to output a measurement image based on the ring-shaped image, and to make the calculation result of the displacement in each divided region correspond to each divided region in the measurement image.

4. The eye refractive power measurement apparatus according to claim 1, wherein
    the calculator is configured to virtually change a relative position of (i) the measured line or the divided approximate curve and (ii) an overall approximate curve, obtained by performing approximate processing on the entire ring-shaped image, in the meridian direction for each divided region,
    the calculator is configured to obtain a state where (i) the measured line or the divided approximate curve and (ii) the overall approximate curve come into contact with or cross each other, and
    the calculator is configured to calculate a displacement between (i) the measured line or the divided approximate curve and (ii) the overall approximate curve in the meridian direction for each divided region in that state.

5. The eye refractive power measurement apparatus according to claim 1, wherein
    the calculator is further configured to calculate a displacement between a center of an ellipse obtained by performing elliptic approximate processing on the entire ring-shaped image, and a center of an ellipse obtained by the divided approximate curve.

6. An error detection apparatus for extracting, as a ring image, reflected light from an examinee's eye and detecting an error region on the examinee's eye, based on the ring image,
    the error detection apparatus comprising:
    a calculator configured to
        acquire a measured line corresponding to an edge of the ring image,
        divide the measured line into predetermined divided regions,
        perform approximate processing on the measured line to calculate an approximate curve,
        calculate a displacement between the measured line and the approximate curve for each divided region of the ring image, and
        detect an error state in each divided region, based on the displacement.

7. An error detection method for extracting, as a ring image, reflected light from an examinee's eye and detecting an error region on the examinee's eye, based on the ring image,
    the error detection method comprising the steps of:
    acquiring a measured line corresponding to an edge of the ring image;
    dividing the measured line into predetermined divided regions;
    performing approximate processing on the measured line to calculate an approximate curve;
    calculating a displacement between the measured line and the approximate curve for each divided region of the ring image; and
    detecting an error state in each divided region, based on the displacement.

8. The eye refractive power measurement apparatus according to claim 1, wherein the calculator is configured to angularly divide the ring-shaped image, with respect to a circumferential direction of the ring-shaped image, into the divided regions.

9. The eye refractive power measurement apparatus according to claim 8, wherein the divided regions extend over equal angle ranges with respect to a center of the ring-shaped image.

10. The error detection apparatus according to claim 6, wherein the calculator is configured to angularly divide the measured line, with respect to a circumferential direction of the ring image, into the divided regions.

11. The error detection apparatus according to claim 10, wherein the divided regions extend over equal angle ranges with respect to a center of the ring image.

12. The error detection method according to claim 7, wherein said dividing comprises angularly dividing the measured line, with respect to a circumferential direction of the ring image, into the divided regions.

13. The error detection method according to claim 12, wherein the divided regions extend over equal angle ranges with respect to a center of the ring image.

* * * * *